US008728144B2

(12) United States Patent
Fearnot

(10) Patent No.: US 8,728,144 B2
(45) Date of Patent: May 20, 2014

(54) ENDOLUMINAL DEVICE INCLUDING A MECHANISM FOR PROXIMAL OR DISTAL FIXATION, AND SEALING AND METHODS OF USE THEREOF

(75) Inventor: Neal E. Fearnot, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1403 days.

(21) Appl. No.: 12/159,142

(22) PCT Filed: Dec. 26, 2006

(86) PCT No.: PCT/US2006/049285
§ 371 (c)(1),
(2), (4) Date: Jun. 25, 2008

(87) PCT Pub. No.: WO2007/079081
PCT Pub. Date: Jul. 12, 2007

(65) Prior Publication Data
US 2009/0043371 A1 Feb. 12, 2009

Related U.S. Application Data

(60) Provisional application No. 60/755,168, filed on Dec. 29, 2005.

(51) Int. Cl.
*A61F 2/06* (2013.01)
(52) U.S. Cl.
USPC ........................................ 623/1.13; 623/1.11
(58) Field of Classification Search
USPC ........... 623/1.13, 1.35, 1.22, 1.18, 1.19, 1.46, 623/1.51
See application file for complete search history.

(56) References Cited

U.S. PATENT DOCUMENTS

| 2,127,903 | A | 8/1938 | Bowen |
| 3,953,566 | A | 4/1976 | Gore |
| 4,502,159 | A | 3/1985 | Woodroof et al. |
| 4,675,361 | A | 6/1987 | Ward, Jr. |
| 4,861,830 | A | 8/1989 | Ward, Jr. |
| 4,902,508 | A | 2/1990 | Badylak et al. |

(Continued)

FOREIGN PATENT DOCUMENTS

| EP | 0 783 874 | 7/1997 |
| WO | WO 98/22158 | 5/1998 |

(Continued)

OTHER PUBLICATIONS

Huynh, T., et al. "Remodeling of an acellular collagen graft into a physiologically responsive neovessel," *Nature Biotechnology*, 17:1083-1086 (1999).

(Continued)

*Primary Examiner* — Tuan V Nguyen
*Assistant Examiner* — Tin Nguyen
(74) *Attorney, Agent, or Firm* — Brinks Gilson & Lione

(57) ABSTRACT

This invention is an endoluminal device including a stent; a tubular graft supported by the stent, wherein the graft comprises a proximal opening and a distal opening; and a variable diameter ring adjacent one of said openings, wherein the variable diameter ring comprises a coiled length of wire having two ends and forming at least one winding around the tubular graft. This invention also relates to the methods of treating an aneurysm and making the endoluminal device.

18 Claims, 11 Drawing Sheets

(56) References Cited

U.S. PATENT DOCUMENTS

| | | | |
|---|---|---|---|
| 5,017,664 | A | 5/1991 | Grasel et al. |
| 5,135,516 | A | 8/1992 | Sahajtian et al. |
| 5,554,389 | A | 9/1996 | Badylak et al. |
| 5,589,563 | A | 12/1996 | Ward et al. |
| 5,711,969 | A | 1/1998 | Patel et al. |
| 5,733,337 | A | 3/1998 | Carr, Jr. |
| 5,755,770 | A * | 5/1998 | Ravenscroft ............ 623/1.13 |
| 5,824,056 | A * | 10/1998 | Rosenberg ............ 623/66.1 |
| 5,961,548 | A | 10/1999 | Shmulewitz |
| 5,980,799 | A | 11/1999 | Martakos et al. |
| 6,149,574 | A * | 11/2000 | Trauthen et al. ............ 600/3 |
| 6,206,931 | B1 | 3/2001 | Cook et al. |
| 6,238,799 | B1 | 5/2001 | Opolski |
| 6,290,720 | B1 * | 9/2001 | Khosravi et al. ............ 623/1.13 |
| 6,358,284 | B1 | 3/2002 | Fearnot et al. |
| 6,379,710 | B1 | 4/2002 | Badylak |
| 6,468,649 | B1 * | 10/2002 | Zhong ............ 428/341 |
| 6,494,904 | B1 * | 12/2002 | Love ............ 623/1.1 |
| 6,547,815 | B2 | 4/2003 | Myers |
| 6,666,892 | B2 | 12/2003 | Hiles et al. |
| 6,695,875 | B2 | 2/2004 | Stelter et al. |
| 6,723,116 | B2 * | 4/2004 | Taheri ............ 623/1.11 |
| 7,306,623 | B2 * | 12/2007 | Watson ............ 623/1.16 |
| 2001/0037142 | A1 | 11/2001 | Stelter et al. |
| 2002/0040238 | A1 * | 4/2002 | Rudnick et al. ............ 623/1.15 |
| 2002/0065552 | A1 | 5/2002 | Jayaraman et al. |
| 2002/0187288 | A1 | 12/2002 | Lim et al. |
| 2003/0114917 | A1 * | 6/2003 | Holloway et al. ............ 623/1.13 |
| 2003/0149471 | A1 | 8/2003 | Briana et al. |
| 2004/0022107 | A1 | 2/2004 | Zaidi et al. |
| 2004/0180042 | A1 | 9/2004 | Cook et al. |
| 2004/0260382 | A1 * | 12/2004 | Fogarty et al. ............ 623/1.11 |
| 2005/0177224 | A1 | 8/2005 | Fogarty et al. |
| 2005/0220848 | A1 | 10/2005 | Bates |
| 2005/0273155 | A1 * | 12/2005 | Bahler et al. ............ 623/1.13 |
| 2006/0009835 | A1 * | 1/2006 | Osborne et al. ............ 623/1.13 |
| 2006/0155359 | A1 * | 7/2006 | Watson ............ 623/1.13 |

FOREIGN PATENT DOCUMENTS

| | | |
|---|---|---|
| WO | WO 98/25636 | 6/1998 |
| WO | WO 98/25637 | 6/1998 |
| WO | WO 98/26291 | 6/1998 |
| WO | WO 98/53761 | 12/1998 |
| WO | WO 00/28921 | 12/2000 |
| WO | WO 2004/022107 | 3/2004 |
| WO | WO 2004022107 A2 * | 3/2004 |

OTHER PUBLICATIONS

Hodde J., "Naturally Occurring Scaffolds for Soft Tissue Repair and Regeneration," *Tissue Engineering*, 8(2):295-308 (2002).

International Standards Organization (ISO) Standard No. 10993 U.S. Pharmacopeia (USP) 23.

U.S. Food and Drug Administration (FDA) blue book memorandum No. G95-1, entitled "Use of International Standard ISO-10993, Biological Evaluation of Medical Devices Part-1: Evaluation and Testing" (1995).

* cited by examiner

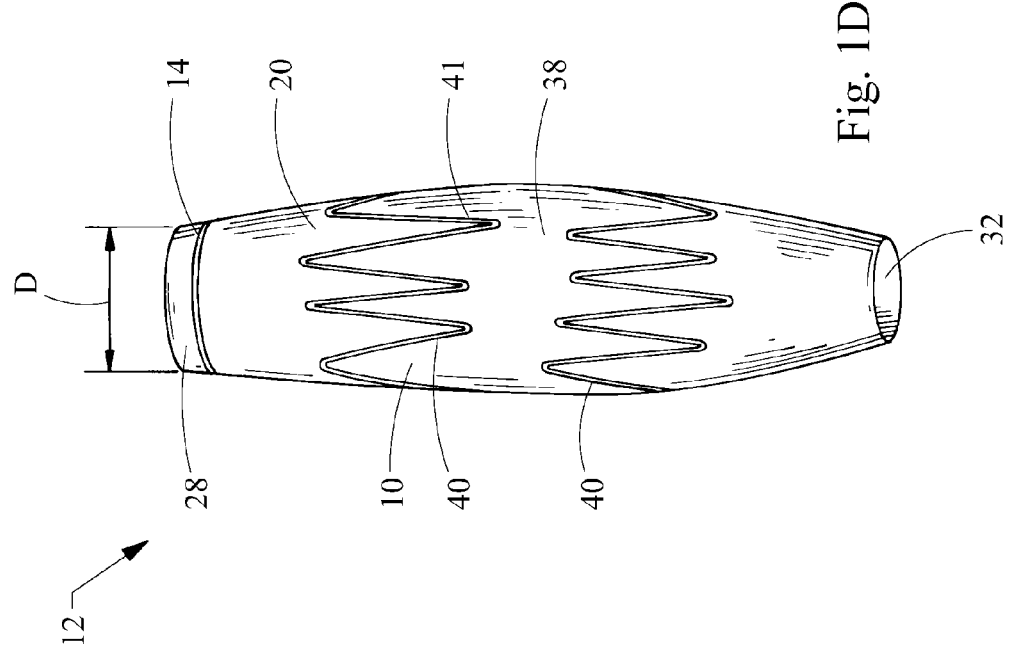
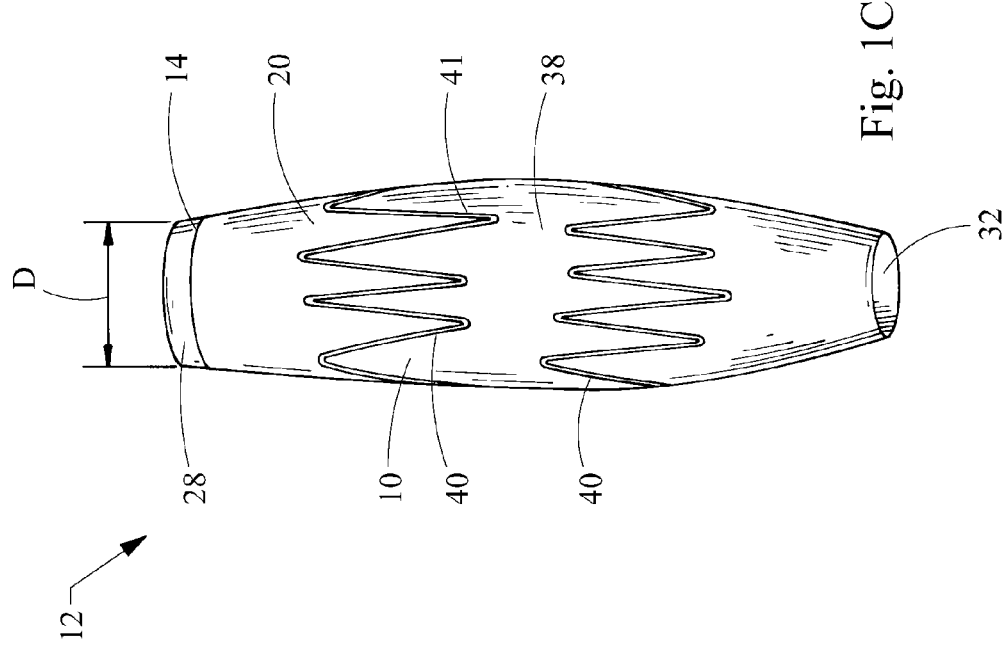

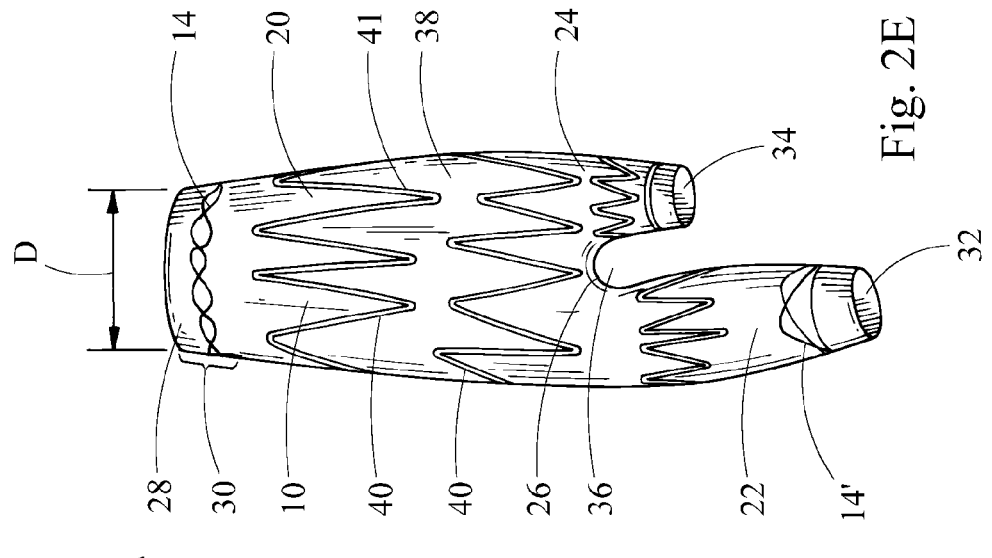
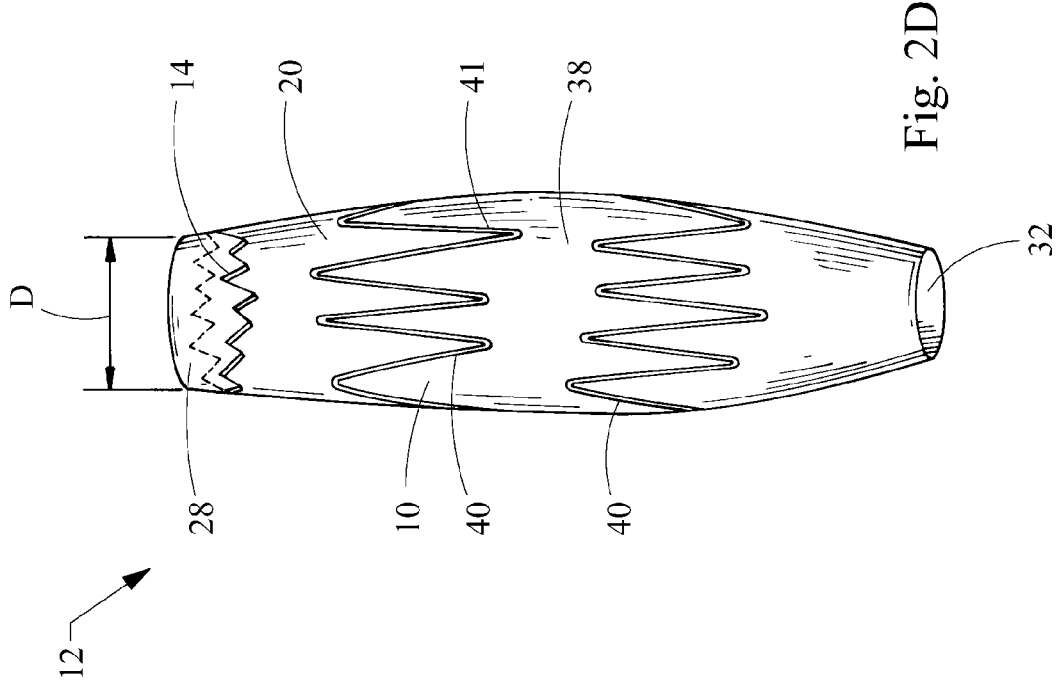

ENDOLUMINAL DEVICE INCLUDING A MECHANISM FOR PROXIMAL OR DISTAL FIXATION, AND SEALING AND METHODS OF USE THEREOF

RELATED APPLICATIONS

The present patent document is §371 filing based on PCT Application Serial No. PCT/US2006/049285, filed Dec. 26, 2006, designating the United States and published in English, which claims the benefit of the filing date under 35 U.S.C. §119(e) of Provisional U.S. Patent Application Ser. No. 60/755,168, filed Dec. 29, 2005. All of the foregoing applications are hereby incorporated by reference.

TECHNICAL FIELD

This invention relates to endoluminal medical devices and methods of use of these devices to treat endovascular disease.

BACKGROUND OF THE INVENTION

The functional vessels of human and animal bodies, such as blood vessels and ducts, occasionally weaken or even rupture. For example, in the aortic artery, the vascular wall can weaken or tear, resulting in dangerous conditions such as aneurysms and dissections. Upon further exposure to hemodynamic forces, such an aneurysm can rupture.

One treatment for aneurysms includes the use of a stent grafts that are placed within the vascular networks and that include one or plural stents affixed to a graft material. The stent grafts are secured at the treatment site by endovascular insertion utilizing inducers and catheters, whereafter they are enlarged radially and remain in place by attachment to the vessel wall. In particular, stent grafts are known for use in treating descending thoracic and abdominal aortic aneurysms where the stent graft at one end defines a single lumen for placement within the aorta and the other end is bifurcated to define two lumens, for extending into the branch arteries. It is important that stent grafts can effectively exclude the aneurysm by sealing both proximally and distally to the aneurysm, such that the patient's blood flow is shunted through the stent graft. A device of this type can, for example, treat various arterial aneurysms, including those in the thoracic aorta, abdominal aorta, iliac, or hypogastric artery.

One example of such a stent graft is disclosed in PCT Publication No. WO 98/53761, in which the stent graft includes a sleeve or tube of biocompatible graft material such as Dacron™ polyester fabric (trademark of E.I. DuPont de Nemours and Co.) or polytetrafluoroethylene defining lumen, and further includes several stents secured therealong, with the stent graft spanning the aneurysm extending along the aorta proximally from the two iliac arteries; the reference also discloses the manner of deploying the stent graft in the patient utilizing an introducer assembly.

Another known stent graft is the Zenith AAA™ stent graft sold by Cook Group Incorporated, Bloomington, Ind.

Stent grafts may be susceptible to certain latent complications, such as instability leading to kinking, obstruction of the lumen and/or disintegration leading to possible graft explantation. The stent graft may undesirably move out of its intended position mostly due to larger displacement forces within the smaller diameter stent graft portions.

Stent grafts may also be susceptible to different types of endoleaks. In some cases, endoleaks allow relapse of the conditions the stent grafts are employed to treat. Endoleaks are sometimes caused or aggrevated by graft migration, in addition to other factors.

Therefore, two closely related aspects of stent graft function are sealing and fixation. Often, a stent graft engages the wall of the lumen on both ends of the aneurysm or other defect, at proximal and distal regions referred to as landing or sealing zones. Typically these sealing zones are located near the termini of the stent grafts. The seal between the stent graft and the vascular wall is typically formed at these locations as a result of the circumferential apposition of the stent graft to the vascular wall, where this apposition is typically maintained by the radial force of the stents that are attached to the stent graft.

It is also desirable to fix, or anchor, the stent graft in place. For some abdominal aortic aneurysm stent grafts, proximal fixation in the neck region of the aorta is critical for long term durability of endoluminal repair.

To date, fixation or anchoring of the stent graft has been achieved using a variety of anchoring mechanisms. For example, one known anchoring mechanism relied on the frictional forces that exist between the stent graft and aortic wall due to the radial force supplied by the stent. Another method of anchoring the stent graft involved tissue incapsulation, wherein exposed stent struts and other parts of the stent graft may eventually become completely encapsulated by tissue growth, thereby assisting fixation.

Fixation was also achieved by fixation at the top or proximal end by barbs or small hooks or by a stent portion that is uncovered by graft material and could be incorporated into the vessel wall. Distal end fixation was attained by friction within the branch or iliac arteries.

In another example of a prior art stent graft described in U.S. Pat. Pub. No. 2001/0037142 A1, graft fixation was achieved by keeping the proximal end of the main stent graft body unattached to the vessel wall and including an attachment tube including an attachment stent for vessel wall attachment at the aneurysm proximal neck, with the attachment tube fully sealing the relative to the aorta while permitting free flow to the renal arteries.

It is therefore important to promote the formation of adequate seal and fixation, especially near the ends of stent graft.

SUMMARY OF THE INVENTION

In one embodiment, the invention is an endoluminal device comprising a stent; a tubular graft supported by the stent, wherein the graft comprises at least a proximal opening and a distal opening; and a variable diameter ring at or adjacent one of said openings, wherein the variable diameter ring comprises a coiled length of wire having two ends and forming substantially at least one winding around the tubular graft. The ring is preferably a nitinol ring. The ring may be a self-expanding ring of a balloon-expandable ring. Preferably, the ring has a plurality of windings. Preferably, the ring has at least about 5 windings. Preferably, the diameter of the wire is in the range of 0.005 to 0.008 cm (0.002 to 0.003 inches) and most preferably substantially 0.063 cm (0.0025 inches). The endoluminal device may further include at least one additional variable diameter ring adjacent one other of said openings. Alternatively a plurality of separate variable diameter rings may be provided at or adjacent a single opening. Preferably, the tubular graft is branched and comprises a second distal opening. Preferably, the stent is a self-expanding stent or a balloon-expandable stent and may be a nitinol stent. Preferably, the endoluminal device of this invention includes a plurality of stents. The tubular graft may include an extracellular matrix material, such as a small intestine submucosa. The device of this invention may further comprise a lubricant.

In another embodiment, the invention is a method for treating an aneurysm, the method comprising delivering an endoluminal device to a location near the aneurysm. The endoluminal device includes a stent; a tubular graft supported by the stent, wherein the graft comprises at least a proximal opening and a distal opening; and a variable diameter ring at or adjacent one of said openings, wherein the variable diameter ring comprises a coiled length of wire having two ends and forming substantially at least one winding around the tubular graft. The aneurysm may be, for example, an aortic abdominal aneurysm.

In yet another embodiment, the invention is a method of making an endoluminal device. The method includes the steps of providing a stent graft wherein the stent graft comprises at least a proximal opening and a distal opening; and attaching a variable diameter ring at or adjacent one of said openings, wherein the variable diameter comprises a coiled length of wire having two ends and forming substantially at least one winding around the stent graft.

In this method, the ring may be a nitinol ring. The method may further include attaching at least one additional variable diameter ring at or adjacent at least one other of said openings.

BRIEF DESCRIPTION OF THE DRAWING

FIG. 1C is another exemplary illustration of an endoluminal device of the present invention;

FIG. 1D is yet another exemplary illustration of an endoluminal device of the present invention;

FIG. 2D is an exemplary illustration of an endoluminal device of the present invention including wire windings in a zig-zag configuration;

FIG. 2E is an exemplary illustration of an endoluminal device of the present invention including crossed-over wires;

DETAILED DESCRIPTION

Figure 1A:
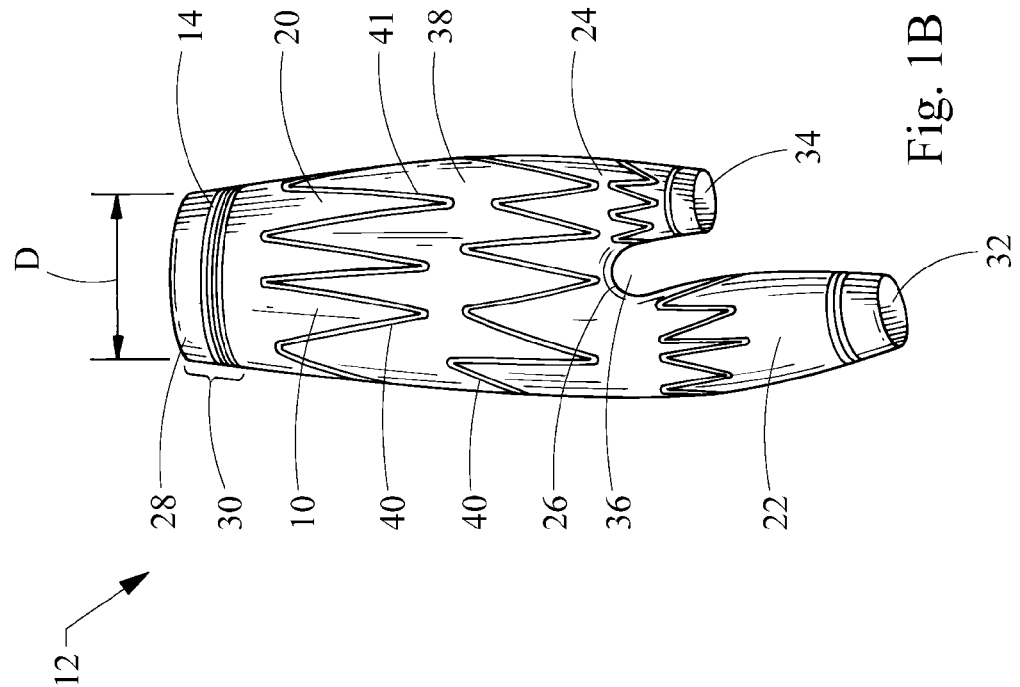
FIG. 1A is an exemplary illustration of an endoluminal device of the present invention.

Unless defined otherwise, all technical and scientific terms used herein have the same meaning as commonly understood to one of ordinary skill in the art to which this invention belongs.

Throughout this specification, when discussing the application of this invention to the aorta, the term "distal" with respect to a device or prosthesis is intended to refer to the end of the device furthest away in the direction of blood flow from the heart, and the term proximal is intended to mean the end of the device that, when implanted, would be nearest to the heart.

The terms "biodegradable" and "bioerodible" refers to something, such graft material, implant, or coating, that when placed the in vivo environment of its intended use will eventually dissolute into constituent parts that may be metabolized or excreted, under the conditions normally present in a living tissue. In exemplary embodiments, the rate and/or extent of biodegradation or bioerosion may be controlled in a predictable manner.

The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" of "endoluminal prosthesis" thus describes devices that can be placed inside one of these lumens.

The term "tubular" refers to the general shape of an endoluminal device which allows the module to carry fluid along a distance or fit within a tubular structure such as an artery. Tubular prosthetic device include single and both, branched and bifurcated devices.

The term "stent" refers to any device or structure that adds rigidity, expansion force or support to a prosthesis when implanted in a body passageway (e.g., a lumen or artery). A stent is used to obtain and maintain the patency of the body passageway while maintaining the integrity of the passageway. Also, the stent may be used to form a seal. The stent may be coated with a polymeric material, for example, by immersion in molten polymer or any other method known to one of skill in the art.

The term "healing" means replacing, repairing, healing, or treating of damaged or diseased tissues of a patient's body.

The terms "patient," "subject," and "recipient" as used in this application refer to any mammal, especially humans.

The present invention provides endoluminal medical devices, including a stent, a tubular graft supported by the stent, wherein the graft comprises a proximal opening and a distal opening. The device also includes a variable diameter ring. Preferably, the variable diameter ring is attached to the graft adjacent to proximal and/or distal openings of the graft. The variable diameter ring comprises a coiled length of wire having two ends and forming at least one winding around the tubular graft. The variable diameter ring(s), once deployed in a vessel, provides a seal of a very short length and fixation between the endoluminal device and the vessel wall as a result of circumferential apposition to the vessel wall, wherein the apposition is maintained by radial force exerted by the variable diameter ring of the device.

In one embodiment, the stent may be formed by a plurality of discontinuous stent elements. In another embodiment, the stent may be formed from a single stent element. The stent may be located on the exterior of the device, the interior of the device, or both. Stent may be balloon-expandable of self-expanding stent. Typically, the stent has a circular cross-section when fully expanded, so as to conform to the generally circular cross-section of a body lumen. In one example, the stent may comprise struts and acute bends or apices that are arranged in a zig-zag configuration in which the struts are set at angles to each other and are connected by the acute bends. The present invention can be used with a wide variety of stent configurations, including, but not limited to shape memory alloy stents, expandable stents, and stents formed in situ.

Preferably, the stent is formed from nitinol, stainless steel, tantalum, titanium, gold, platinum, inconel, iridium, silver, tungsten, cobalt, chromium, or another biocompatible metal, or alloys of any of these. Examples of other materials that may be used to form stents, include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. Preferably, the stent is a nitinol or stainless steel stent.

The term "stent graft" refers to a type of endoluminal device made of a tubular graft material and supported by at least one stent.

The tubular graft material is preferably constructed from a biocompatible material. The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible graft, when introduced into a majority of patients, will not cause a significantly adverse, long-lived or escalating biological reaction or response, and is distinguished from a mild, transient inflammation which typically accompanies surgery or implantation of foreign objects into a living organism.

The tubular graft material may be constructed from a biocompatible textile fabric, a polymer, biomaterial, or a composite thereof. Examples of various graft materials are described below.

As mentioned above, the tubular graft material may be constructed from a biocompatible textile fabric. Examples of biocompatible materials from which textile graft material can be formed include polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile graft, provided the final textile is biocompatible. Textile materials that can be formed into fibers suitable for making textile grafts include polyethylene, polypropylene, polyaramids, polyacrylonitrile, nylons and cellulose, in addition to polyesters, fluorinated polymers, and polyurethanes as listed above. Preferably the textile is made of one or more polymers that do not require treatment or modification to be biocompatible. The graft is preferably constructed from a material such as woven multifilament polyester. One example of biocompatible polyester include Dacron™ (DuPONT, Wilmington, Del.), which is known to be sufficiently biologically inert, non-biodegradable, and durable to permit safe insertion inside the human body. Polyester is also known to excite fibrous ingrowth which will secure the graft to the wall of the lumen within a few months of its insertion. Any material with such qualities may be used, however.

One example of suitable stent graft is disclosed in PCT Publication No. WO 98/53761, in which the stent graft includes a sleeve or tube of biocompatible graft material such as Dacron™, which is incorporated herein in its entirety.

The tubular graft material may be also constructed from a polymer. Examples of biocompatible materials from which a polymer graft material can be formed include other polyesters, such as polylactide, polyglycolide and copolymers thereof; fluorinated polymers, such as polytetrafluoroethylene (PTFE), expanded PTFE and poly(vinylidene fluoride) discussed above; polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Other suitable polymers include polyolefins, polyacrylonitrile, nylons, polyaramids and polysulfones, in addition to polyesters, fluorinated polymers, polysiloxanes, and polyurethanes as listed above. Preferably the graft material is made of one or more polymers that do not require treatment or modification to be biocompatible.

More preferably, the graft includes a biocompatible polyurethane. Examples of biocompatible polyurethanes include THORALON (THORATEC, Pleasanton, Calif.), BIOSPAN, BIONATE, ELASTHANE, PURSIL and CARBOSIL (POLYMER TECHNOLOGY GROUP, Berkeley, Calif.).

Most preferably, the polymer graft contains the polyurethane THORALON. As described in U.S. Pat. Pub. No. 2002/0065552 A1, incorporated herein by reference, THORALON is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A polymer graft material can be formed from these two components by dissolving the base polymer and additive in a solvent such as dimethylacetamide (DMAC) and solidifying the mixture by solvent casting or by coagulation in a liquid that is a non-solvent for the base polymer and additive.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON may be useful in larger vessels, such as the abdominal aorta, where elasticity and compliance is beneficial.

In addition to THORALON, other polyurethane ureas may be used as the graft material. For example, the BPS-215 component with a MDI/PTMO mole ratio ranging from about 1.0 to about 2.5 may be used.

In addition to polyurethane ureas, other polyurethanes, preferably those having a chain extended with diols, may be used as the graft material. Polyurethanes modified with cationic, anionic and aliphatic side chains may also be used. See, for example, U.S. Pat. No. 5,017,664. Polyurethanes may need to be dissolved in solvents such as dimethyl formamide, tetrahydrofuran, dimethyacetamide, dimethyl sulfoxide, or mixtures thereof.

In addition, the polyurethanes may also be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

In one embodiment, the graft material may contain a polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. Examples of siloxane-polyurethanes are disclosed in U.S. Pat. Pub. No. 2002/0187288 A1, which is incorporated herein by reference.

The graft may contain polytetrafluoroethylene or expanded polytetratfluoroethylene (ePTFE). The structure of ePTFE can be characterized as containing nodes connected by fibrils. The structure of ePTFE is disclosed, for example, in U.S. Pat. Nos. 6,547,815 B2; 5,980,799; and 3,953,566; all of which are incorporated herein by reference.

If so desired, the polymers described above can be processed to form porous polymer grafts using standard processing methods, including solvent-based processes such as casting, spraying and dipping, and melt extrusion processes. Extractable pore forming agents can be used during processing to produce porous polymer graft material. Examples of the particulate used to form the pores include a salt, including, but not limited to, sodium chloride (NaCl), sodium bicarbonate (NaHCO$_3$), Na$_2$CO$_3$, MgCl$_2$, CaCO$_3$, calcium fluoride (CaF$_2$), magnesium sulfate (MgSO$_4$), CaCl$_2$, AgNO$_3$ or any water soluble salt. However, other suspended particulate materials may be used. These include, but are not limited to, sugars, polyvinyl alcohol, cellulose, gelatin or polyvinyl pyrolidone. Preferably, the particulate is sodium chloride; more preferably, the particulate is a sugar.

Pore forming agents may have a particle size from about 10 μm to about 500 μm, from about 20 μm to about 100 μm, and from about 10 μm to about 40 μm. The amount of pore forming agent relative to the polymer may be from about 20 percent by weight (wt %) to about 90 wt %, and from about 40 wt % to about 70 wt %. These sizes and amounts of pore forming agents can provide for a high degree of porosity following extraction of the pore forming agent. The porosity can be from about 20 wt % to about 90 wt %, and from about 40 wt % to about 70 wt % of the final product.

For example, formation of porous THORALON is described in U.S. Pat. Pub. Nos. 2003/0114917 A1 and 2003/0149471 A1, both of which are incorporated herein by reference.

Examples of other materials from which the graft can be formed include biomaterials, such as naturally occurring polymeric scaffolds, bioscaffolds, biomatrices, ECM scaffolds, or naturally occurring biopolymers.

These biomaterials can be selected from a variety of commercially available matrices including collagen matrices, or can be prepared from a wide variety of natural sources of collagen. Examples of these naturally occurring biomaterials include submucosa, acellular dermis, cadaveric fascia, the bladder acellular matrix graft, and amniotic membrane (for review see Hodde J., Tissue Engineering 8(2):295-308 (2002), which is incorporated by reference in its entirety). In addition, collagen-based extracellular matrices derived from renal capsules of warm blooded vertebrates may be selected as a graft. The extracellular matrices derived from renal capsules of warm blooded vertebrates were described in WO 03/02165, the disclosure of which is incorporated herein by reference.

Another type of biomaterial, isolated from liver basement membrane, is described in U.S. Pat. No. 6,379,710, which is incorporated herein by reference. Biomaterial may also be isolated from pericardium, as described in U.S. Pat. No. 4,502,159, which is also incorporated herein by reference.

In addition to xenogenic biomaterials, autologous tissue can be harvested as well. Additionally elastin or elastin-like polypeptides (ELPs) and the like offer potential as a biologically active ECM. Another alternative would be to use allographs such as harvested native valve tissue. Such tissue is commercially available in a cryopreserved state.

Juvenile submucosa tissue from warm blooded vertebrates, such as a porcine mammal, may also be used. Juvenile submucosal tissue was described in WO 04/22107, the disclosure of which is incorporated herein by reference.

"Tela submucosa" or "submucosa," which refers to a layer of collagen-containing connective tissue occurring under the mucosa in most parts of the alimentary, respiratory, urinary and genital tracts of animals, may also be used. Submucosa would be a preferred source of biomaterial and has been previously described in U.S. Pat. Nos. 6,206,931, 6,358,284 and 6,666,892 as a biocompatible, non-thrombogenic material that enhances the repair of damaged or diseased host tissues. U.S. Pat. Nos. 6,206,931, 6,358,284 and 6,666,892 are incorporated herein by reference. The submucosa may be derived from intestine. The mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389, the disclosures of all are expressly incorporated herein.

The submucosa is preferably derived from the intestines, more preferably the small intestine, of a warm blooded vertebrate; i.e., small intestine submucosa (SIS). SIS is commercially available from Cook Biotech, West Lafayette, Ind. Preferred intestine submucosal tissue typically includes the tunica submucosa delaminated from both the tunica muscularis and at least the luminal portions of the tunica mucosa. In one example the submucosal tissue includes the tunica submucosa and basilar portions of the tunica mucosa including the lamina muscularis mucosa and the stratum compactum. The preparation of intestinal submucosa is described in U.S. Pat. No. 4,902,508, and the preparation of tela submucosa is described in U.S. Pat. No. 6,206,931, both of which are incorporated herein by reference. The preparation of submucosa is also described in U.S. Pat. No. 5,733,337 and in 17 Nature Biotechnology 1083 (November 1999); and WIPO Publication WO 98/22158, dated 28 May 1998, which is the published application of PCT/US97/14855. Also, a method for obtaining a highly pure, delaminated tela submucosa collagen matrix in a substantially sterile state was previously described in U.S. Pat. Pub. No. 20040180042, disclosure of which is incorporated by reference.

It is also possible to form large surface area constructs by combining two or more submucosa sections using techniques described in U.S. Pat. Nos. 2,127,903 and 5,711,969, which are incorporated herein by reference. Thus, a plurality of submucosa strips can be fused to one another, for example by compressing overlapping areas of the strips under dehydrating conditions, to form an overall planar construct having a surface area greater than that of any one planar surface of the individual strips used to form the construct.

The purified submucosa can be conditioned, as described in U.S. Pat. No. 6,206,931, to alter the viscoelastic properties of the purified submucosa. The purified submucosa may be conditioned by stretching, chemically treating, enzymatically treating or exposing the matrix structure to other environmental factors. In one embodiment, the strips of purified tela submucosa may be conditioned by stretching in a longitudinal and/or lateral direction to a strain of no more than 20%. Strain is the percentage increase in the length of the material after loading.

In another embodiment, the purified submucosa may be conditioned by stretching the material longitudinally to a length longer than the length of the purified submucosa from which the biomaterial was formed. The conditioning process and other relevant processes are described in U.S. Pat. No. 6,358,284 which is incorporated herein by reference.

The graft may be made from other biomaterials, including acellular dermis, cadaveric fascia, bladder acellular matrix, and amniotic membrane previously described in U.S. Pat. Pub. No. US 2005-0220848 A1, disclosure of which is incorporated by reference, and other available biomaterials.

Figure 1B:
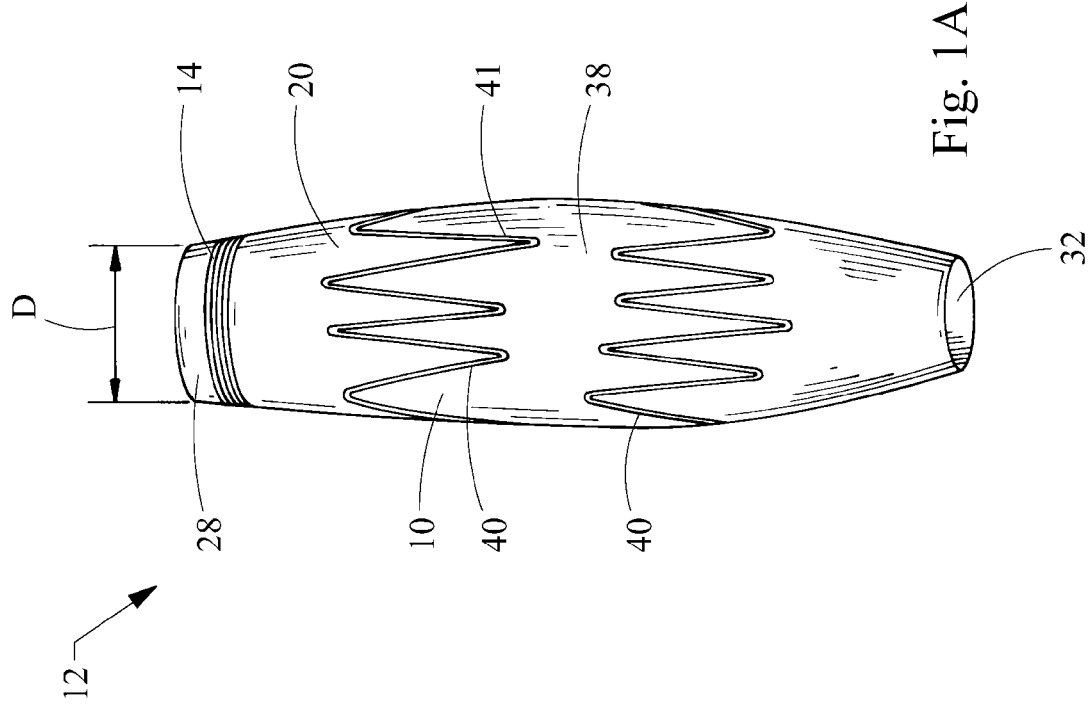
FIG. 1B is an exemplary illustration of a bifurcated endoluminal device of the present invention.

As shown in FIGS. 1A and 1B in a fully expanded state, if unconstrained within a vessel or delivery catheter, the endoluminal device of the present invention 12 includes a stent 41 and a tubular graft 20 supported by the stent 41. The graft comprises a proximal opening 28 and a distal opening 32. The stent and the tubular graft form a stent graft 10. The endoluminal device further comprises a variable diameter ring 14 adjacent one, any two or all three of the openings 28, 32 and 34, wherein the variable diameter ring 14 comprises a coiled length of wire having two ends and forming at least one winding around the tubular stent graft 10. As shown in FIG. 1A, the wire may form a plurality of windings around the tubular stent graft 10.

In other embodiments shown in FIGS. 1C and 1D, the endoluminal device 12 includes a variable diameter ring 14 adjacent opening 28, wherein the variable diameter ring 14 comprises a coiled length of wire having two ends and forming one (FIG. 1C) or two (FIG. 1D) winding(s) around the tubular stent graft 10.

Each individual opening 28, 32 and/or 34 may have a plurality of separate variable diameter rings placed at or adjacent thereto.

In one embodiment, especially shown in FIG. 1B, the endoluminal device may be a branched device and includes a stent graft 10 comprising an integral ipsilateral leg and a contralateral stump that together define a bifurcation at the distal end. A known stent graft that may be suitable for used as a main stent graft of endoluminal device of the present invention is the Zenith AAA™ stent graft sold by Cook Group Incorporated, Bloomington, Ind., United States and William A. Cook Australia Pty., Brisbane, Australia Preferably, as shown in FIG. 1B, the stent graft 10 includes a primary graft section 20, an ipsilateral leg 22 and a contralateral limb or stump 24. Primary graft section 20 is disposed within the aneurysm and extends from the bifurcation 26 to a proximal end 28 of proximal end portion 30, and has a lumen with a relatively constant diameter D that approximates the diameter of a healthy section of the aorta, generally about 26 mm. Ipsilateral leg 22 is associated with the ipsilateral iliac artery and extends to a distal end 32. Contralateral stump 24 is associated with the contralateral iliac artery and coextends a short distance from bifurcation 26 to a distal end 34; preferably, it is spaced from ipsilateral leg 22 a distinct small gap 36 therefrom for the length of the contralateral stump.

The endoluminal device of this invention also includes a variable diameter ring 14 adjacent to the proximal 28, and/or distal 32 and 34, or all openings of the graft, as shown in FIG. 1B.

The variable diameter ring 14 may be a balloon-expandable ring or self-expanding. The ring is preferably manufactured from a single length of a superelastic or shape memory alloy, such as Nitinol, a nickel-titanium alloy, or stainless steel wire having two ends and coiled around the circumference of the stent graft 10. The wires may also be made from other shape memory metals, such as alloys of Cu—Zn—Al or Cu—Al—Ni. Other suitable materials for the rings are cobalt, chromium, a polymer or a photo-curable material. Very thin wires are preferred, such as wires having a diameter of about 0.0025 inches (about 0.063 mm). Round wires are preferred, but wires of any shape may be used, including rectangular wire, square wire, wedge or "pie-shaped" wire, flat wire and triangular wire. Each "wire" in reality may comprise two or more wires twisted together for greater stiffness and control of the device.

Figure 2A:
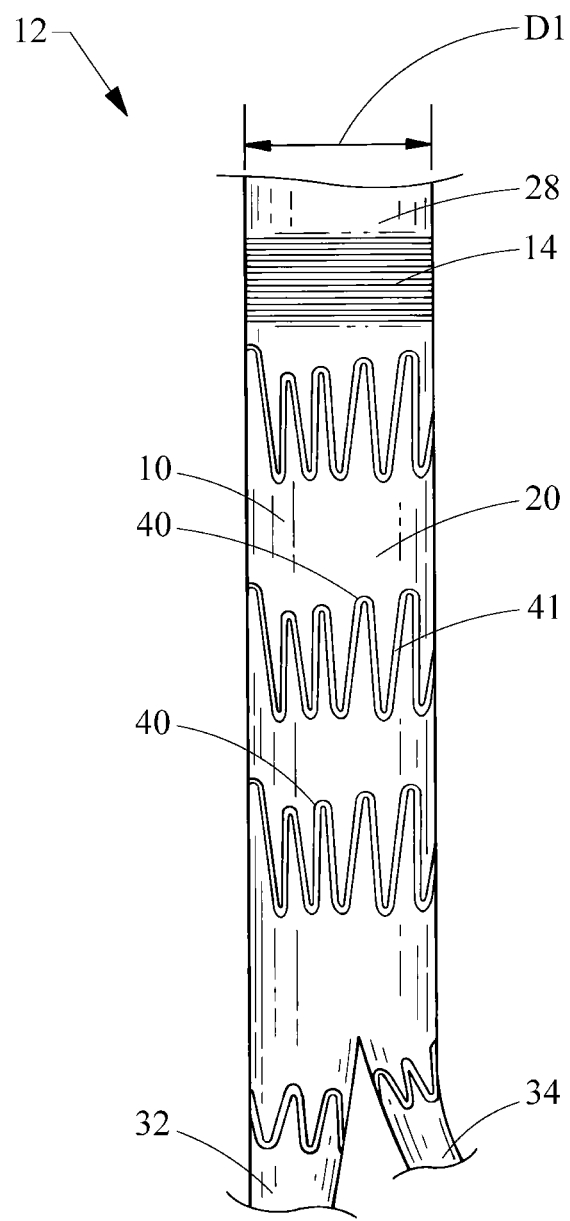
FIG. 2A is an exemplary illustration of a bifurcated endoluminal device of the present invention in a compressed state.

In the pre-deployment stent graft 10, as shown in FIG. 2A, the ring 14 has smaller diameter D1 so that is can fit into an appropriate deployment sheath (compressed state). The small-diameter D1 ring is made by winding the wire segment multiple times around an appropriately constricted stent graft 10. Alternatively, the wire may be wrapped around a stent graft in its expanded diameter; the wire is then cinched to reduce the ring diameter. Any excess wire may be removed before insertion of the stent graft into the delivery sheath. A sufficient length of wire is used, however, so that in the deployment stent graft, the ring has a predetermined number of windings after the stent graft is expanded.

Figure 2B:
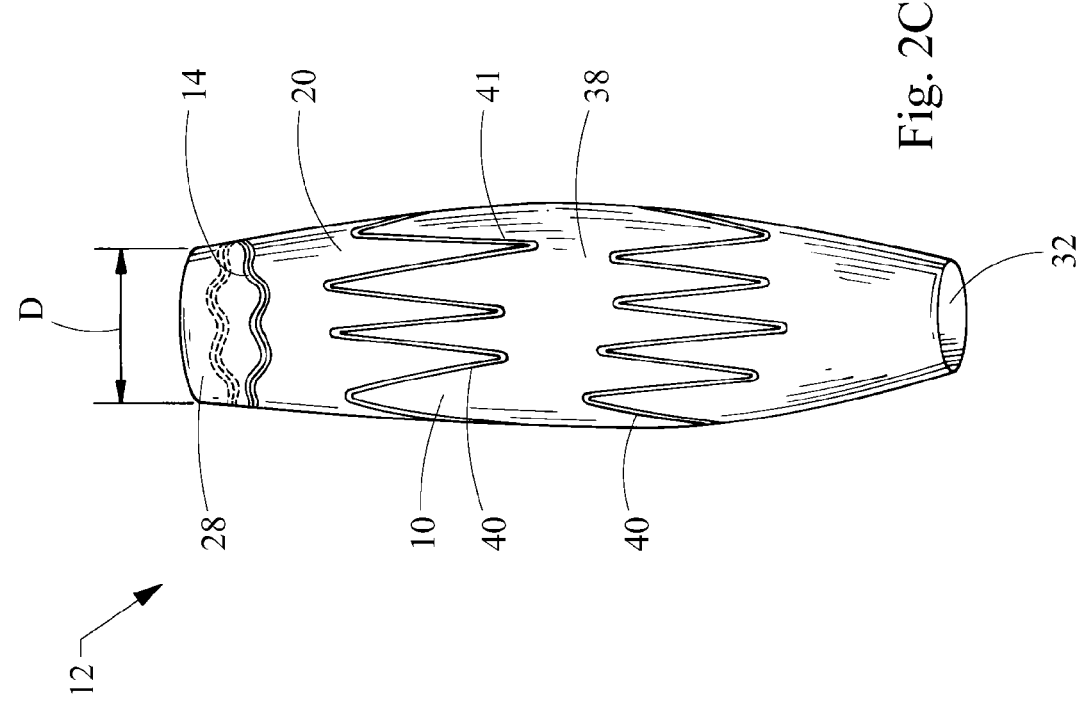
FIG. 2B is an exemplary illustration of an endoluminal device of the present invention including circular windings of a wire.
Figure 2C:
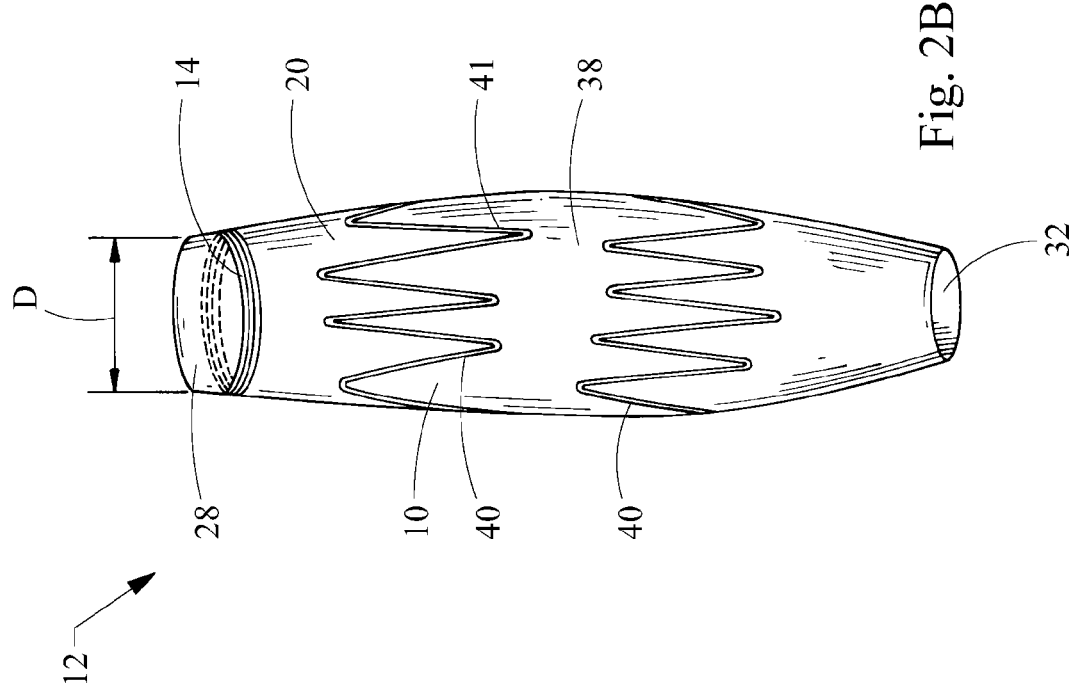
FIG. 2C is an exemplary illustration of an endoluminal device of the present invention including wire windings in sine wave configuration.

As illustrated in FIGS. 2B-D, once expanded, the ring 14 may be have a circular configuration (2B), or configuration that is irregular, such as sine wave (2C), zig-zag (2D), or other suitable configuration. The wires of the ring 14 and 14' may also cross each other over, as shown in FIG. 2E. All ring configurations described above may be compressible to a smaller pre-deployment stent configuration.

The number of initial windings may be calculated based on the expansion ratio from the stent graft that is fully compressed in the delivery system to the stent graft that is fully expanded in diameter, times the number of loops or windings desired in the expanded state. For example, if 3 windings of wire are desired in the final expansion state of the stent graft to provide a sufficient radial force against the vessel wall; and if the expanded stent graft diameter D is 30 mm; and the compressed stent graft diameter D1 is 18 Fr or 6 mm, the expansion ratio is 30/6 or 5; then the number of windings needed in the compressed state is 3×5 equals 15 windings. Therefore, the initial wire length needed is greater than 51 windings×Pi($\pi$)×30 mm (expanded diameter), which is 1413 mm or 14.13 cm. Once the stent graft is compressed for delivery, 15 windings remain and excess wire may be cut off. The remaining wire length is equal to 15 windings×$\pi$×6 mm; i.e., 283 mm. Once expanded the stent graft will have 3 windings.

Preferably, at least 1 winding or turn of the wire remains after delivery of the stent graft. However, there suffices a length of wire forming just less than one complete winding or turning, i.e. between 85 and 100% of a complete turn. More preferably, at least 3 windings or turns remain after delivery of the stent graft. Most preferably, at least 5 windings or turns remain after delivery of the stent graft. A plurality of windings or turns is preferred.

Figure 3A:
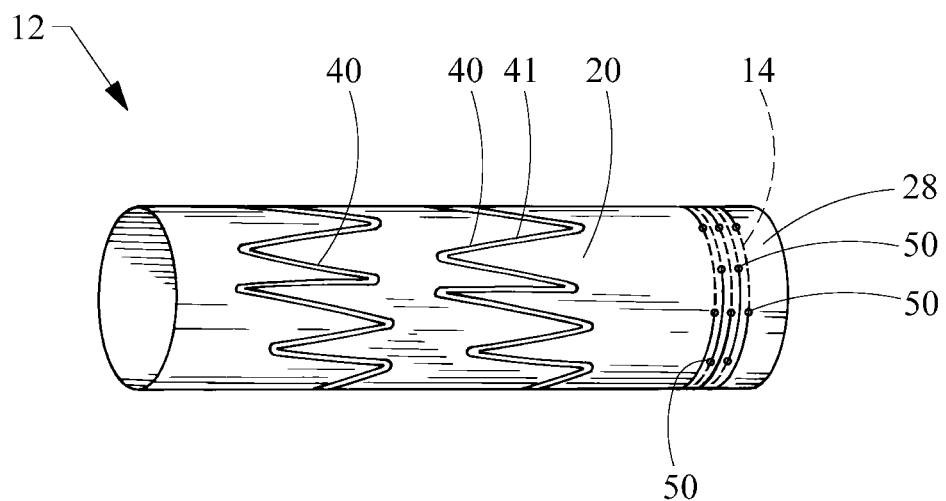
FIG. 3A illustrates one embodiment of the present invention.

To retain the wire in the proximity of graft, wire 14 may be attached to the graft material by an attachment mechanism. For example, as illustrated in FIG. 3A, the proximal end 28 of the stent graft may include channels, holes, or fenestrations 50 through which the wire is weaved or tied to the graft material 20.

Figure 3B:
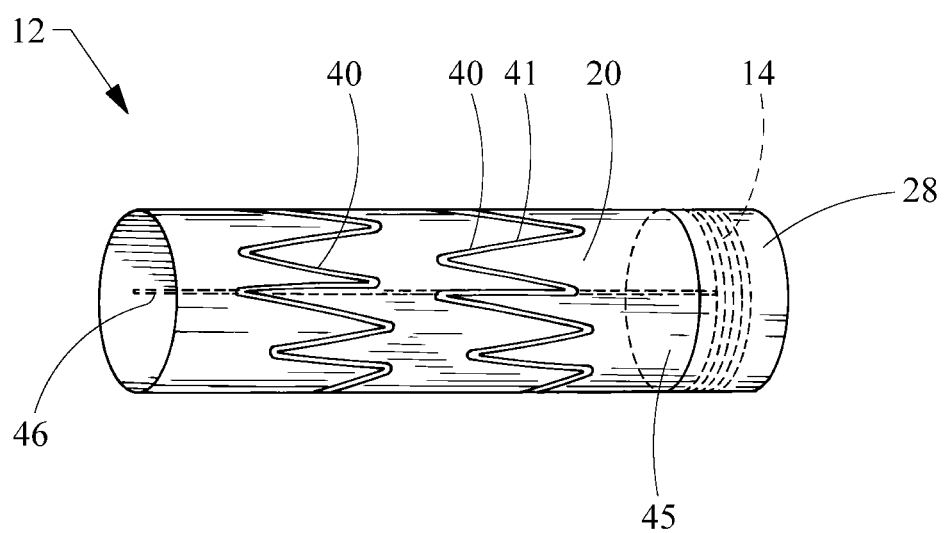
FIG. 3B illustrates another embodiment of the present invention.
Figure 3C:
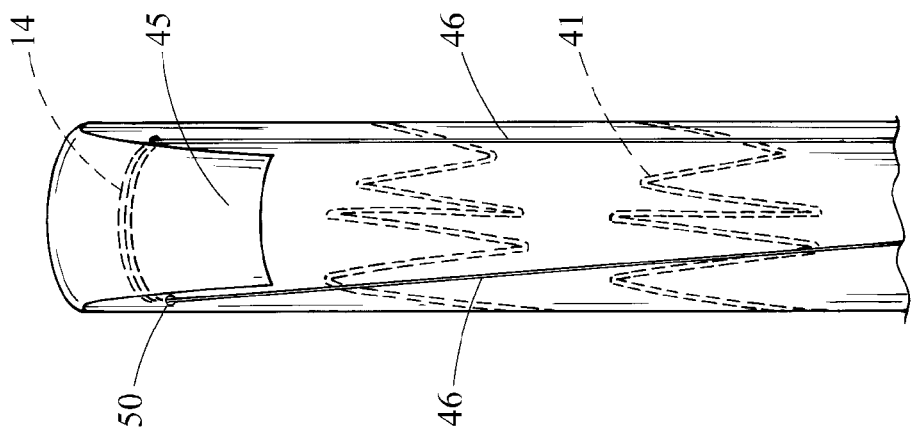
FIG. 3C illustrates yet another embodiment of the present invention.
Figure 3D:
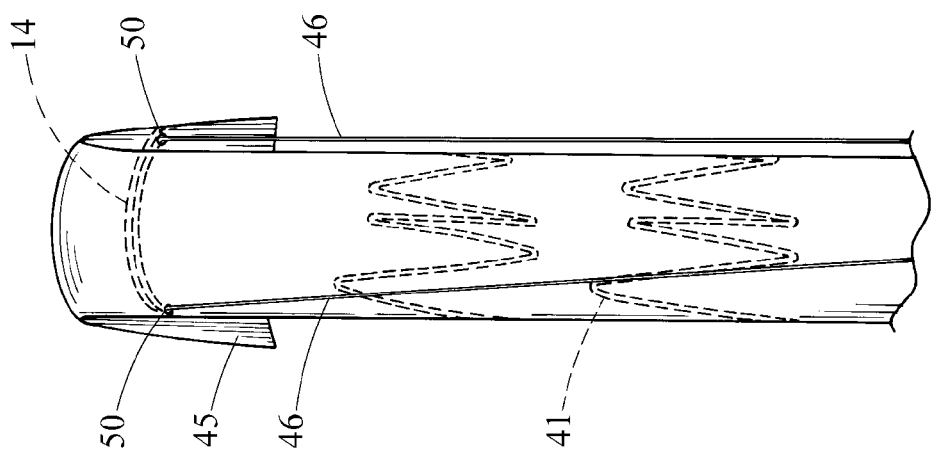
FIG. 3D illustrates another embodiment of the present invention.

In one embodiment, shown in FIGS. 3B-3D, the wire ring 14 may be covered by a cuff 45 in the graft material 20 and one or both ends of the wire may extend through the hole 50 in the cuff 45. The cuff 45 may be an external cuff (FIG. 3C) or an internal cuff (FIG. 3D). The hole 50, depending on the position of the cuff 45, may be on the inside at the lumen or on the outside of the graft, so that the length of the wire 46 would extend towards the outside or down the lumen. Preferably, the length of the wire 46 extends down the lumen. Preferably, the wire will have enough expansion force in the windings of the wire to pull the end or ends of the wire into the cuff as it self-expands upon deployment in the vessel.

Figure 3E:
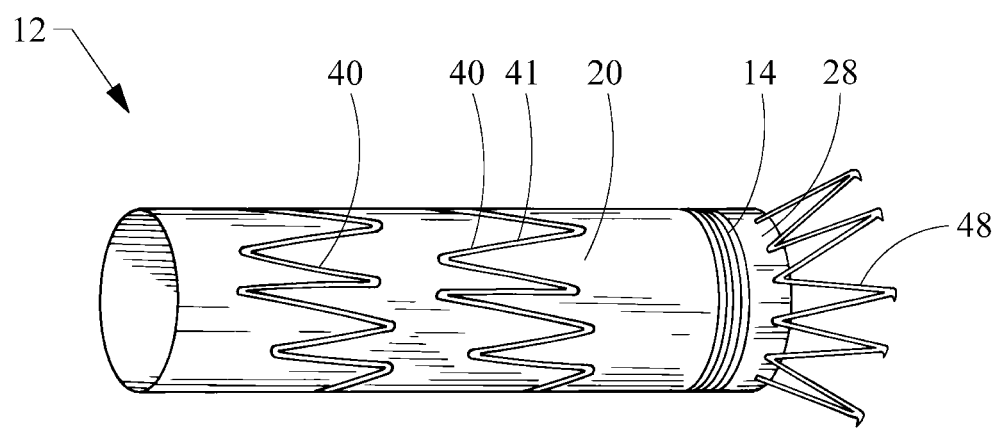
FIG. 3E illustrates yet another embodiment of the present invention.
Figure 3F:
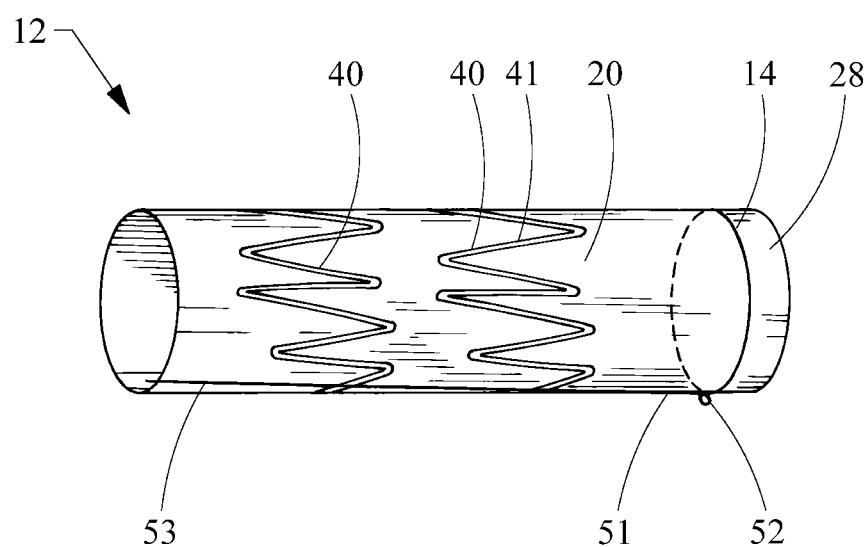
FIG. 3F illustrates yet another embodiment of the present invention.

To ensure that the ends of the wire (head and tail) are aligned as the winding forms upon the expansion or the wire, in one embodiment illustrated in FIG. 3F, the head of the wire winding 51 may have a loop 52 through which the tail end 53 of the wire passes. A plurality of loops may be present along the length of the wire.

In one embodiment, a lubricant may be applied to the wire prior to deployment in the vessel to reduce friction and to assist with the self-expansion process of the wire windings described above. The lubricant may be a hydrophilic coating, such as LubriLAST™, which is available from Advance Surface Technology, Billerica, Mass. LubriLAST™ has been previously described in U.S. Pat. No. 6,238,799, disclosure of which is incorporated herein in its entirety. Examplary lubricious hydrophilic coatings and methods of bonding them were previously described in U.S. Pat. No. 5,135,516, which is incorporated by reference in its entirety. Other suitable hydrophilic coatings may also be used and will be known to those skilled in the art. Hydrophillic coatings are preferred as lubricious coatings for the wire. Hydro-Silk™ is an example of a hydrophobic-hydrophilic coating that increases lubricity when dry, and also provides increased lubricity when introduced into a fluid environment. Lubricants would also enable a greater number of windings of the wire to be employed in the cuff 45. Other available coatings that may reduce friction and assist with the expansion process of the wire windings, include, but are not limited to, teflon, paralene, and other suitable coatings.

In one embodiment, as shown in FIG. 3E, the endoluminal device of this invention may further include a typical attachment stent, including barbs or small hooks 48 at the proximal end of the device 12.

Figure 4A:
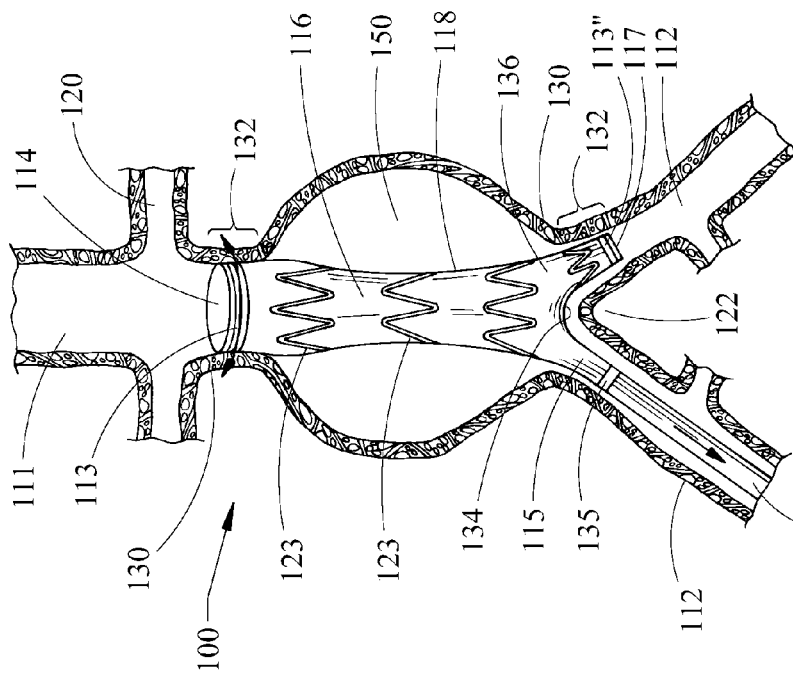
FIG. 4A is an exemplary illustration of bifurcated endoluminal device of the present invention being positioned and deployed in the aneurysm.
Figure 4B:
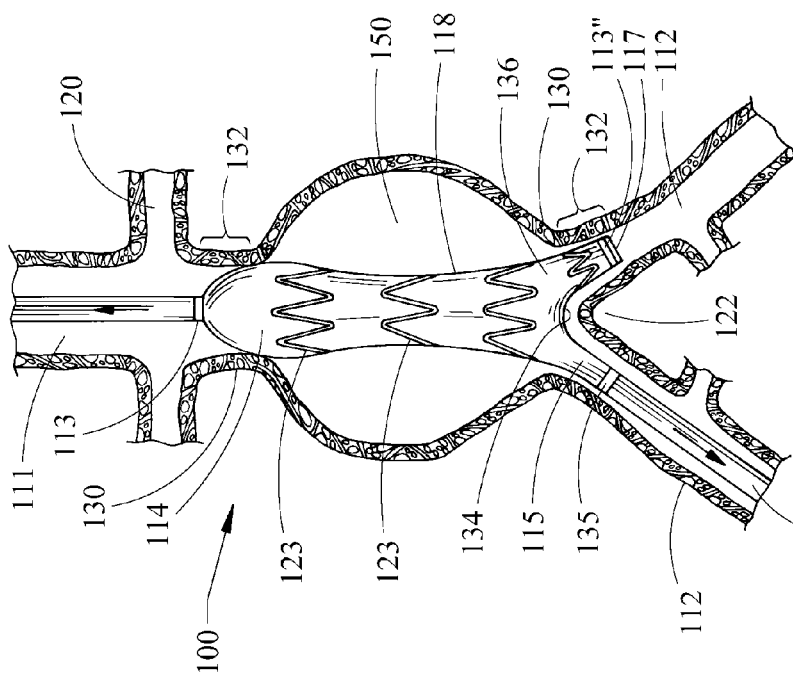
FIG. 4B is another exemplary illustration of bifurcated endoluminal device of the present invention being positioned and deployed in the aneurysm
Figure 4C:
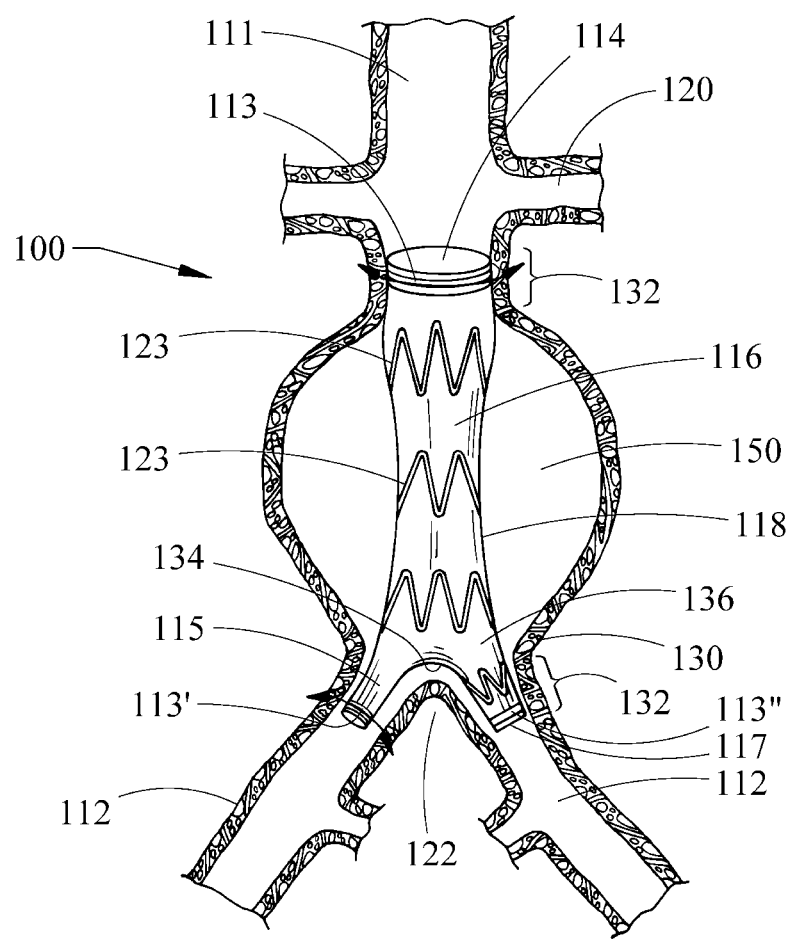
FIG. 4C is another exemplary illustration of bifurcated endoluminal device of the present invention being positioned and deployed in the aneurysm.

Once deployed in a vessel, as shown in FIGS. 4A-4C, the device of this invention is attached to the vessel wall by radial force that the ring exerts on the stent graft and the surrounding vessel wall, which keeps the graft open and promotes vascular apposition (arrows). One of the surprising and unexpected advantages of this fixation and sealing device is that it has a very narrow profile, and is thus suited to deployment in shorter vessel lengths.

In a preferred embodiment, shown in FIGS. 4A-4C, a modular bifurcated stent graft 100 is deployed within an aneurysmal aorta 111 and both iliac arteries 112. The stent graft includes a variable diameter ring 113 at the proximal end 114 and two variable diameter rings 113' and 113" at distal ends 115 and 117, respectively, of the stent graft that anchor (i.e., affix) the stent graft to the healthier, preferably non-aneurysmal tissue 130 near the renal arteries and in iliac arteries. The graft 116 that make up the stent graft 100 are generally tubular, so that the fluid can flow through the stent graft 100, and are preferably made of biocompatible polyurethane, polysiloxane, polyester, fluorinated polymer; or a textile, such as poly(ethylene terephthalate) or similar materials described above. The main body 118 extends from the renal arteries 120 to near the bifurcation 122. Preferably, the main body 118 has a proximal lumen about 24 mm in diameter and extending about 50 mm in length to the bifurcation 134. The ipsilateral leg 135 is about 12 mm in diameter and continues along a length about 80 mm from the bifurcation 134 to a flared distal end or cuff about 16 to 18 mm in diameter when unconstrained. A contralateral stump 136 coextends along the ipsilateral leg and also has a diameter of about 12 mm with a length of about 35 mm. Preferably, the length of the contralateral stump 136 is spaced from the ipsilateral leg 135 so it is easily fitted over and seated against the bifurcation 134 of the vessel at the iliac arteries 112, when the main stent graft body 118 is pulled distally after partial deployment, that is, wherein the contralateral stump exits the delivery sheath (see FIG. 5) and is deflected laterally upon expansion of stents 40 that have also exited the sheath after the sheath has been partially withdrawn distally.

Preferably, multiple self-expanding Z-stents 123 are secured along the length of the stent graft 100. Self-expanding stents 123 may be secured to and along the graft material either along the outer surface or inner surface of the graft material such as by sutures, direct attachment to the graft material, such as by heating the stent to melt and form thermoplastically fused regions that adhere to the graft (described in U.S. Patent Application Ser. No. 60/755,708, entitled "Direct Attachment of a Stent to a Graft Material," disclosure of which is incorporated herein in its entirety), or other suitable method.

Two iliac extension modules (not shown) may extend from the iliac limbs 133.

The stent graft 100 will preferably achieve a blood-tight seal through the variable diameter ring at the contact regions 132 on both ends of the aneurysm 150, so that the aneurysm 150 will be excluded. In the particular embodiments shown in FIGS. 4A-4C, the stent graft 100 contacts the vascular tissue below the renal arteries 120, around the bifurcation 122 and at the iliac limbs 130 and extensions (not shown). In this embodiment, a seal is preferably achieved that will help exclude the entire aneurysmal region and, as a result, the hemodynamic pressures within the aneurysm 150 may be reduced.

In FIG. 4A, the proximal end 114, including self-expandable variable diameter ring 113 of the endoluminal device, is first retained by the cylindrical sleeve 151, as discussed in great detail below. In FIGS. 4A and 4B, the distal ipsilateral end is retained within the external sheath 152.

In all the embodiments, the variable diameter rings may form the ends of the grafts, that is the rings may be at the openings themselves. The present invention also includes an illustrative method of inserting an endoluminal device of this invention in an aneurysm utilizing the device delivery system described below.

Now, with reference to FIG. 5, general deployment of the endoluminal device of the present invention will now be described.

Figure 5:
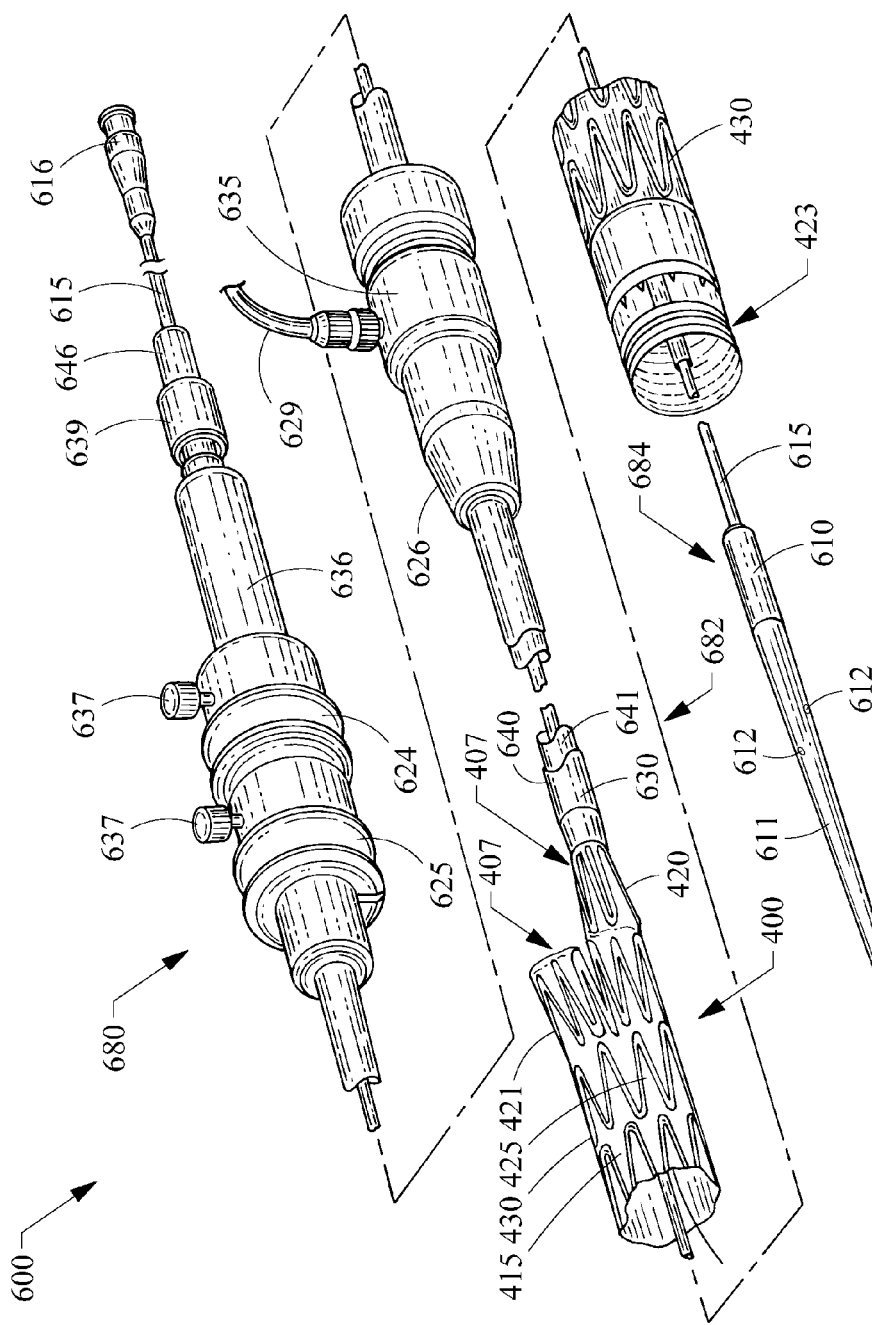
FIG. 5 is a perspective view of a bifurcated endoluminal device of the present invention in combination with an endovascular deployment system or introducer.

FIG. 5 shows a perspective view of exemplary endoluminal device of the present invention 400, including a variable diameter wire 423, in combination with an endovascular deployment system or introducer 600. Although a variety of delivery techniques and apparatuses may be employed to deploy the device 400, in a preferred embodiment the introducer 600 is employed. The introducer 600 is described in greater detail in PCT application WO98/53761, which is incorporated in its entirety.

The introducer 600 includes an external manipulation section 680, a distal attachment region 682 and a proximal attachment region 684. The distal attachment region 682 and the proximal attachment region 684 secure the distal ends 407 and the proximal end 406, respectively. During the medical procedure to deploy the device 400, the distal and proximal attachment regions 682 and 684 will travel through the lumen to a desired deployment site. The external manipulation section 680, which is acted upon by a user to manipulate the introducer, remains outside of the patient throughout the procedure.

The proximal attachment region 684 of the introducer 600 includes a cylindrical sleeve 610. The cylindrical sleeve 610 has a long tapered flexible extension 611 extending from its proximal end. The flexible extension 611 has an internal longitudinal aperture (not shown). This longitudinal aperture facilitates advancement of the tapered flexible extension 611 along an insertion wire (not shown). The longitudinal aperture also provides a channel for the introduction of medical reagents. For example, it may be desirable to supply a contrast agent to allow angiography to be performed during placement and deployment phases of the medical procedure.

A thin-walled metal tube 615 is fastened to the extension 611. The thin-walled metal tube 615 is flexible so that the introducer 600 can be advanced along a relatively tortuous vessel, such as a femoral artery, and so that the distal attachment region 682 can be longitudinally and rotationally manipulated. The thin-walled metal tube 615 extends through the introducer 600 to the manipulation section 680, terminating at a connection means 616.

The connection means 616 is adapted to accept a syringe to facilitate the introduction of medical reagents into the thin-walled metal tube 615. The thin-walled metal tube 615 is in fluid communication with the apertures 612 of the flexible extension 611. Therefore, medical reagents introduced into connection means 616 will flow to and emanate from the apertures 612.

A plastic tube 641 is coaxial with and radially outside of the thin-walled metal tube 615. The plastic tube 641 is "thick-walled"—its wall is preferably several times thicker than that of the thin-walled metal tube 615. A sheath 630 is coaxial with and radially outside of the plastic tube 641. The thick-walled plastic tube 641 and the sheath 630 extend distally to the manipulation region 680.

During the placement phase of the medical procedure, the device 400 is retained in a compressed condition by the sheath 630. The sheath 630 extends distally to a gripping and hemostatic sealing means 635 of the external manipulation section 680. During assembly of the introducer 600, the sheath 630 is advanced over the cylindrical sleeve 610 of the proximal attachment region 684 while the device 400 is held in a compressed state by an external force. A distal attachment (retention) section 640 is coupled to the thick-walled plastic tube 641. The distal attachment section 640 retains the distal ends 407, optionally including distal variable diameter rings, of the device 400 during the procedure. Likewise, the cylindrical sleeve 610 retains the proximal end of the device 400, including the variable diameter ring 423. The distal ends 407 of the device 400 have a loop (not shown) through which a distal trigger wire (not shown) extends. The distal trigger wire extends through an aperture (not shown) in the distal attachment section 640 into an annular region between the thin-walled tube 615 and the thick-walled tube 641. The distal trigger wire extends through the annular space to the manipulation region 680. The distal trigger wire exits the annular space at a distal wire release mechanism 625.

The external manipulation section 680 includes a hemostatic sealing means 635. The hemostatic sealing means 635 includes a hemostatic seal (not shown) and a side tube 629. The hemostatic sealing means 635 also includes a clamping collar 626 that clamps the sheath 630 to the hemostatic seal, and a silicone seal ring (not shown) that forms a hemostatic seal around the thick-walled plastic tube 641. The side tube 629 facilitates the introduction of medical reagents between the thick-walled tube 641 and the sheath 630.

A proximal portion of the external manipulation section 680 includes a release wire actuation section that has a body 636. The body 636 is mounted onto the thick-walled plastic tube 641. The thin-walled tube 615 passes through the body 636. The distal wire release mechanism 625 and the proximal wire release mechanism 624 are mounted for slidable movement onto the body 636.

The positioning of the proximal and distal wire release mechanisms 624 and 625 is such that the proximal wire release mechanism 624 must be moved before the distal wire release mechanism 625 can be moved. Therefore, the distal ends 407 of the device 400 cannot be released until the proximal end with the variable diameter ring 422 has been released, and the ring affixed to the lumen of the vessel. Clamping screws 637 prevent inadvertent early release of the device 400. A hemostatic seal (not shown) is included so that the release wires can extend out through the body 636 without unnecessary blood loss during the medical procedure.

A distal portion of the external manipulation section 680 includes a pin vise 639. The pin vise 639 is mounted onto the distal end of the body 636. The pin vise 639 has a screw cap 646. When screwed in, vise jaws (not shown) of the pin vise 639 clamp against or engage the thin-walled metal tube 615. When the vise jaws are engaged, the thin-walled tube 615 can only move with the body 636, and hence the thin-walled tube 615 can only move with the thick-walled tube 641. With the screw cap 646 tightened, the entire assembly can be moved together as one piece.

The device 400 is preferably inserted by an introducer 600 via percutaneous entry femoral artery, and then advanced into the desired position over a stiff wire guide using endoluminal interventional techniques. For example, a guide wire (not shown) is first introduced into a femoral artery of the patient and advanced until its tip is beyond the desired deployment region of the device 400. At this stage, the introducer assembly 600 is fully assembled, and ready for introduction into the patient. The device 400 is retained at one end by the cylindrical sleeve 610 and the other by the distal attachment sections 640, and compressed by the sheath 630. In addition, the introducer assembly 600 can be inserted through a femoral artery over the guide wire, and positioned by radiographic techniques, which are not discussed here.

Once the introducer assembly 600 is in the desired deployment position, the sheath 630 is withdrawn to just proximal of the distal attachment section 640. This action releases the middle portion of the device 400 so that it can expand radially. The proximal end of the device 400, including the variable diameter ring 423, however, is still retained within the cylindrical sleeve 610 and the distal ends 407, which may also include variable diameter ring(s) are still retained within the external sheath 630.

Next, the pin vise 639 is released to allow small movements of the thin-walled tube 615 with respect to the thick-walled tube 641. These movements allow the device 400 to be lengthened or shortened or rotated or compressed for accurate placement in the desired location within the lumen. Radiopaque markers (not shown) may be placed along the device 400 to assist with placement of the device.

When the proximal end 406 of the device 400 is in place, the proximal trigger wire is withdrawn by distal movement of the proximal wire release mechanism 624. The proximal wire release mechanism 624 and the proximal trigger wire can be completely removed by passing the proximal wire release mechanism 624 over the pin vise 639, the screw cap 646, and the connection means 616. Next, the screw cap 646 of the pin vise 639 is loosened, after which the thin-walled tube 615 can be pushed in a proximal direction to move the cylindrical sleeve 610 in a proximal direction. When the cylindrical sleeve 610 no longer surrounds the variable diameter ring 422, the self-expanding ring 423 expands. When the ring 423 expands, the ring affixes to the walls of the lumen to hold the proximal end 206 in place. From this stage on, the proximal end 406 of the device 400 cannot be moved again.

Once the proximal end 406 is anchored, the external sheath 630 is withdrawn to distal of the distal attachment section 640. This withdrawal allows the shorter leg 421 and the longer leg 420 of the device 400 to expand. At this point, the distal ends 407 of the device 400 may still be moved. Consequently, the device 400 can still be rotated or lengthened or shortened for accurate positioning. Such positioning of the device 400 may ensure that the shorter leg 421 extends in the direction of a contralateral artery. In one embodiment, when the distal ends include variable diameter rings, the proximal ends are placed in exact position before release from the external sheath. Upon releasing, the external sheath no longer surrounds the variable diameter rings, the self-expanding rings expand. When the rings expand, the rings affix to the walls of the lumen to hold the distal ends in place.

The introducer 600 and the deployment method described above can be adapted for implantation in other regions. In addition, a simpler variation of the introducer 600 may be used to introduce the endoluminal device, including variable diameter ring, of this invention. This simpler variation of the introducer 600 may be based on the same principles as the introducer 600 described above, but may be less complex.

This method of deployment provides for the exact placement of the endoluminal device of this invention at a location in a patient's body. Another example of delivery system and method of delivering endoluminal devices, including extensions, was previously described in U.S. Pat. No. 6,695,875 B2, which is incorporated in its entirety.

In one embodiment, the invention is directed to a method for treating endovascular disease, such as aneurysm. The method comprises delivering an endoluminal implantable medical device comprising a stent; a tubular graft supported by the stent, wherein the graft comprises a proximal opening and a distal opening; and a variable diameter ring adjacent one of said openings, wherein the variable diameter ring comprises a coiled length of wire having two ends and forming at least one winding around the tubular graft. The device may be used to treat, for example, an abdominal aortic aneurysm.

The device may be advanced into the patient using conventional techniques such as over a guiding catheter with an advancing catheter or element as described above.

The remaining details of the method of medical treatment are the same as those disclosed with respect to the method of delivering the device of the present invention; for the sake of brevity, they need not be repeated here.

In addition, the invention concerns a kit comprising an endoluminal implantable medical device, comprising a stent; a tubular graft supported by the stent, wherein the graft comprises a proximal opening and a distal opening; and a variable diameter ring adjacent one of said openings, wherein the variable diameter ring comprises a coiled length of wire having two ends and forming at least one winding around the tubular graft. Preferably, the ring includes a plurality of windings. The kit also includes a mechanism capable of inserting the device into a lumen of a body, wherein the device is the device as disclosed above. In an aspect, the invention relates to these kits wherein the mechanism is an intraluminal catheter.

The kit may further include instructional materials.

It is therefore intended that the foregoing detailed description be regarded as illustrative rather than limiting, and that it be understood that it is the following claims, including all equivalents, that are intended to define the spirit and scope of this invention.

The invention claimed is:

1. An endoluminal device, comprising:
    a stent;
    a tubular graft supported by the stent, wherein the graft comprises at least a proximal opening and a distal opening; and
    a variable diameter ring at or adjacent at least one of said openings, wherein the variable diameter ring comprises a coiled length of wire having two ends and forming substantially at least one winding around the tubular graft, wherein the coiled length of wire has a head end and a tail end, the head end having a loop through which the tail end of the wire passes.

2. The endoluminal device of claim 1, wherein the ring is a nitinol ring.

3. The endoluminal device of claim 1, wherein the ring is a self-expanding ring or a balloon-expandable ring.

4. The endoluminal device of claim 1, wherein the ring has a plurality of windings.

5. The endoluminal device of claim 4, wherein the ring has at least five windings.

6. The endoluminal device of claim 1, wherein the wire has a diameter in the range from about 0.005 cm to about 0.008 cm (about 0.002 inches to about 0.003 inches).

7. The endoluminal device of claim 1, further comprising at least one additional variable diameter ring at or adjacent both of said openings.

8. The endoluminal device of claim 1, wherein the stent is a self-expanding stent or a balloon-expandable stent.

9. The endoluminal device of claim 1, wherein the stent is a nitinol stent.

10. The endoluminal device of claim 1, comprising a plurality of stents.

11. The endoluminal device of claim 1, wherein the tubular graft comprises an extracellular matrix material.

12. The endoluminal device of claim 11, wherein the extracellular matrix material is a small intestine submucosa material.

13. The endoluminal device of claim 1, further comprising a lubricant, wherein the lubricant is applied to the coiled length of wire.

14. The endoluminal device of claim 1, further comprising a hydrophilic coating.

15. The endoluminal device of claim 1, wherein the variable diameter ring is covered by a cuff in the tubular graft.

16. The endoluminal device of claim 15, wherein the cuff is an external cuff or an internal cuff.

17. An endoluminal device comprising:
    a stent;
    a branched tubular graft supported by the stent, wherein the graft comprises at least a proximal opening and two distal openings; and
    a variable diameter ring at or adjacent at least one of said openings, wherein the variable diameter ring comprises a coiled length of wire having two ends and forming substantially at least one winding around the tubular graft, wherein the coiled length of wire has a head end and a tail end, the head end having a loop through which the tail end of the wire passes.

18. An endoluminal device, comprising:
    a stent;
    a tubular graft supported by the stent, wherein the graft comprises at least a proximal opening and a distal opening, the endoluminal device having a compressed state and an expanded state; and
    a variable diameter ring at or adjacent at least one of said openings, wherein the variable diameter ring comprises a coiled length of wire having two ends and forming substantially at least one winding around the tubular graft in the expanded state, wherein the coiled length of wire has a head end and a tail end, the head end having a loop through which the tail end of the wire passes,
    wherein an initial number of windings of the variable diameter ring in the compressed state is a product of an expansion ratio and a number of windings in the expanded state;
    wherein the expansion ratio is a ratio of an expanded stent graft diameter by a compressed stent graft diameter; and
    wherein a length of wire is equal to a result of multiplying the number of initial wire windings by Pi ($\pi$) and by the expanded stent graft diameter.

* * * * *